United States Patent [19]

Clark et al.

[11] Patent Number: 4,609,667

[45] Date of Patent: * Sep. 2, 1986

[54] INHIBITOR OF MAMMALIAN COLLAGENASE AND ELASTASE

[75] Inventors: Donald E. Clark, Norristown; Norman H. Grant, Wynnewood, both of Pa.

[73] Assignee: American Home Products Corporation, New York, N.Y.

[ * ] Notice: The portion of the term of this patent subsequent to Jan. 28, 2003 has been disclaimed.

[21] Appl. No.: 714,309

[22] Filed: Mar. 21, 1985

Related U.S. Application Data

[63] Continuation of Ser. No. 562,807, Dec. 19, 1983, abandoned, which is a continuation-in-part of Ser. No. 505,517, Jun. 17, 1983, abandoned.

[51] Int. Cl.$^4$ ............................................. A61K 31/425
[52] U.S. Cl. ..................................................... 514/367
[58] Field of Search ........................................ 514/367

[56] References Cited

U.S. PATENT DOCUMENTS 4,247,535  1/1981  Lewis et al. .......................... 424/180
4,367,233  1/1983  Clark et al. .......................... 514/367

OTHER PUBLICATIONS

Chemical Abstracts, vol. 43 (1949), #47100; Neuberg et al.
Chemical Abstracts, vol. 82 (1975), #103136w; Kawata.
Chemical Abstracts, vol. 91 (1979), #125092s; Onczul.
Chemical Abstracts, vol. 94 (1981), #36376g; Christiansen.
Rohdewald, P., et al., *Thermochimica Acta*, 49, 101–110 (1981).

*Primary Examiner*—Leonard Schenkman
*Assistant Examiner*—Joseph A. Lipovsky
*Attorney, Agent, or Firm*—George Tarnowski

[57] ABSTRACT

A method of inhibiting mammalian elastase and collagenase by using [benzothiazolylthio]phenylacetyl-L-cysteines and the pharmaceutically acceptable salts thereof.

2 Claims, No Drawings

INHIBITOR OF MAMMALIAN COLLAGENASE AND ELASTASE

This is a continuation of application Ser. No. 562,807 filed Dec. 19, 1983, now abandoned, which is a continuation-in-part of Ser. No. 505,517, filed June 17, 1983, now abandoned.

BACKGROUND OF THE INVENTION

Collagen is the major organic component of the surface tissue found in the cornea, skin, gastro-intestinal viscera, joint mucosa and other areas of the body. The collagen molecule has a molecular weight of 300,000, and is composed of three helical polypeptide chains which are wound around a common axis forming a coiled chain. In solution collagen molecules exist as long rods about 300×15 A, but at a temperature of 37° C. and a pH of 7, the molecules polymerize into insoluble fibrils. Thus, it is as fibrils that collagen invariably exists in tissue. The helical structure of undenatured collagen is remarkably resistant to attack by proteolytic enzymes; however, there have been discovered a number of natural enzymes, i.e., animal collagenases, which are capable of breaking down collagen by cleaving the collagen molecule across the helical backbone yielding ¾ and ¼ length fragments.

Similarly, elastin is a significant component of the elastic fibers of connective tissue, being found particularly in joints, the ligaments of the vertebrae, the walls of the large arteries and in the connective tissue of the lungs. The polymeric structure of elastin contains large amounts of glycine, alanine and valine residues, and its elastic properties are brought about by the cross-linking of the amino acids in its structure. Elastin is broken down by the protease elastase, which is capable of hydrolyzing proteins at the N-terminal peptide bond of aliphatic amino acid residues.

The relationship between collagenase and the destruction of collagen-based tissue has been found in a number of disease states affecting various parts of the body, all of which are basically similar in that collagen constitutes the major organic component, e.g., skin, cornea, gastro-intestinal viscera, joint mucosa, etc. For example, in connection with corneal tissue, it has been shown that collagenase is responsible for ulcers appearing after the eye ha been burned with alkali. Similarly, the relationship exists for other ulcerous conditions of the cornea such as viral ulcers, e.g. herpes simplex, vaccinia, etc.; bacterial ulcers, e.g. Pseudomonas, etc.; degenerative ulcers and ulcers of unknown origin, e.g., associated with rheumatoid arthritis, Mooren's ulcer, furrow ulcer; and ulcers secondary to drying, e.g. erythema multiforme (Stevens-Johnson syndrome).

In mammals, collagenase is one of the key enzymes involved in the cartilage and joint destruction of rheumatoid arthritis; see, for example, *Arthritis and Rheumatism*, 20 (6):1231 (1977). Further, recent research results have been reported (*Pharmacology International*, 2, p. 11–16 (1982)) which support the conclusion that the destruction of human articular cartilage proceeds through the joint action of the enzymes elastase and collagenase. Elastase degrades the proteoglycans which along with collagen cross-linking provide a barrier to the action of collagenase on collagen. Elastase also solubilizes collagen, eliminating the cross-linking portion of the collagen fibrils, permitting the collagen to then be more completely degraded by both elastase and collagenase. Thus, both elastase and collagenase are key factors in the joint cartilage destruction found in rheumatoid arthritis.

The action of mammalian collagenase has also been implicated as a causative factor in several other diseases in mammals. These diseases include periodontal disease, tumor invasiveness, and epidermolysis bullosa; see, for example, *American Journal of Pathology*, 92 (2): 509 (1978) and *The New England Journal of Medicine*, 291 (13): 652 (1974).

The action of mammalian elastase, likewise, has been determined to be a causative factor in other disease states. Thus, the first step in the disease process of emphysema has been shown to be the breakdown of lung elastin into small peptides. The unchecked destruction of lung connective tissue elastin by elastase results in the enlargement of distal air spaces and destruction of alveolar cell walls. The healthy lung is protected from the destructive effects of elastase by normal levels of the naturally occuring elastase inhibitor, $\alpha_1$-antitrypsin. If the level of $\alpha_1$-antitrypsin falls below about 80 mg/dL, such as occurs in individuals afflicted with emphysema, elastase begins to destroy the lungs. Therefore, the exogenous administration of an elastase inhibitor to supplement the low levels of endogenous $\alpha_1$ antitrypsin is indicated in the treatment of emphysema [see *Journal of the American Medical Association*, 249(22), 3007 (1983)].

Accordingly, collagenase/elastase inhibitors can be advantageously used to block pathologies in which destruction of collagen- and elastin-containing connective tissue plays a central role, such as for example, periodontal disease, rheumatoid arthritis, emphysema, corneal ulcerations, and so forth.

DESCRIPTION OF THE INVENTION

The present invention is directed to a method of inhibiting mammalian collagenase/elastase in mammals afflicted with a disease state in which collagen- or elastin-containing tissue is broken down by elastase and collagenase which comprises administering to such an afflicted mammal an amount sufficient to inhibit said elastase/collagenase-induced collagen breakdown of an elastase/collagenase inhibitor having the formula:

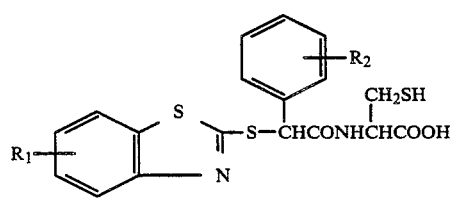

I wherein $R_1$ is hydrogen, halo, nitro, amino, lower alkyl, lower alkoxy, trifluoromethyl or hydroxy; $R_2$ is fluorine, chlorine, bromine, lower alkyl lower alkoxy, amino, nitro or trifluoromethyl; and the pharmacologically acceptable salts thereof.

The compounds of formula I and their method of preparation are disclosed in pending U.S. Ser. No. 413,275.

The term "lower alkyl" when used herein includes straight and branched chain hydrocarbon radicals having from 1 to about 6 carbon atoms. The term "lower alkoxy" designates radicals in which the hydrocarbon portion has 1 to about 6 carbon atoms.

The term "halo" when used herein refers to radicals of the elements fluorine, chlorine and bromine.

The term pharmaceutically acceptable salts includes the salts of pharmacologically-acceptable organic and inorganic acids such as hydrochloric, hydrobromic, sulfuric, nitric, phosphoric, methanesulfonic, benzenesulfonic and the like, alkali metal carboxylates and carboxylates of a pharmacologically acceptable cation derived from ammonia or a basic amine.

The compounds of the invention are most conveniently prepared by reacting the tricyclic mesoionic didehydro compounds disclosed in U.S. Pat. No. 4,275,065 with appropriate nucleophilic reactants. This reaction, involving the ring cleavage of the terminal thiazole ring, is as follows:

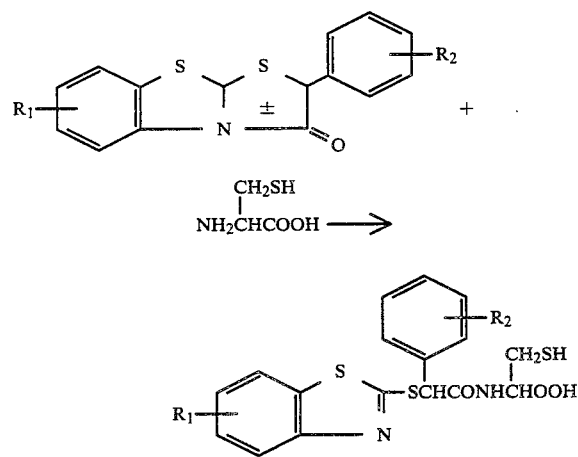

wherein $R_1$ and $R_2$ are as described hereinbefore. The reaction is carried out in a suitable organic solvent, such as for example methylene chloride, and over a range of temperatures, such as room temperature as well as under reflux conditions.

The term "pharmacologically acceptable carrier" contemplates usual and customary substances employed to formulate solid, oral unit dosages for pharmacological purposes, including in its broadest form animal feedstuff. It also includes those employed to formulate either in unit dose or multidose form, oral and injectable suspensions and solutions, either directly or for reconstitution before administration.

To formulate dosages for administration according to this invention the compounds of formula I can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacanth, methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases the proportion of active ingredients in said compositions both solid and liquid will be at least sufficient to impart collagenase inhibitory activity thereto on oral or parenteral administration.

In practicing the method of the invention, the instant compositions can be administered to warm-blooded animals, e.g., mice, rats, rabbits, dogs, horses, monkeys, anthropoid apes, and the like, in a variety of dosage forms, alone or in combination with pharmacologically effective carriers, preferably orally or by injection.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for injection administration the dose is from about 25 milligrams to about 50 milligrams and for oral administration the dose is from about 50 milligrams to about 200 milligrams and preferably from about 50 milligrams to about 100 milligrams per day either as a single unit dose, or if desired, the dosage may be divided into convenient subunits administered at convenient times throughout the day.

The ability of the compounds of the invention to inhibit elastase and collagenase is demonstrated by testing in an enzyme assay using collagenase produced by normal human leukocytes or by normal human fibroblasts in culture and in an enzyme assay using human leukocyte elastase.

The following examples show the preparation and testing of a compound used in the invention.

N-[[(5-chloro-2-benzothiazolyl)thio]phenylacetyl]-L-cysteine

A. α-(5-Chlorobenzothiazol-2-ylthio)benzene acetic acid 50.0 g. (0.248 m) 5-chloro-2-mercaptobenzothiazole and 53.0 g. (0.248 m) α-bromophenylacetic acid are dissolved in 1.5 l. acetone and the solution is heated for 4 hours in the presence of 50 ml. glacial acetic acid. The solution is concentrated to a smaller volume (about 200 ml) and the residual solid (90 g.) is collected. The resulting salt is suspended in 1 l of water and the mixture is stirred at room temperature overnight. The collected solid is recrystallized from 2.5 l. acetonitrile to give a total of 64 g (85% yield) of title compound melting at 190°-2° C.

Analysis for: $C_{15}H_{10}ClNO_2S_2$, Calculated: C, 53.64; H, 3.00; N, 4.17, Found: C, 53.83; H, 3.13; N, 4.13.

B.
6-Chloro-2-phenylthiazolo[2,3-b]benzothiazol-3(2$\underline{H}$)-one mesoionic didehydro derivative 31 g. (0.092 m) of the compound of A. above is suspended in 3.5 l. methylene chloride and the mixture is heated to gentle reflux in the presence of 25 ml. acetic anhydride. The solid is gradually dissolved, the solution turning reddish. After heating overnight, the solution is filtered and concentrated to 200 ml. The residual orange solid, weighing 29.5 g. (quantitative yield), is collected and has a melting point of 215°–6° C.

C.
N-[[(5-Chloro-2-benzothiazolyl)thio]phenylacetyl-L-cysteine 6.36 g. (0.02 m) of the compound of B. above, 2.4 g. (0.02 m) L-(−)-cysteine and 2.5 g. (0.025 m) triethylamine are suspended in methylene chloride (800 ml) and the mixture is heated for 56 hours. After filtering off some insoluble material, the filtrate is washed with dilute hydrochloric acid solution and then dried over anhydrous magnesium sulfate. The oily residue left after solvent removal is triturated with ether and the solid is collected. The ether solution, upon standing, yields more solid. The combined solids are recrystallized from acetonitrile to give 1.5 g. (17% yield) of the title compound, which has a melting point of 155°–8° C.

Analysis for: $C_{18}H_{15}ClN_2O_3S_3$, Calculated: C, 49.25; H, 3.44; N, 6.38, Found: C, 49.36; H, 3.45; N, 6.0.

EXAMPLE 2

The compound N-[[(5-chloro-2-benzothiazolyl)thio]-phenylacetyl]-L-cysteine is tested for collagenase inhibition in an in vitro assay based on the procedure described by A. Sellers and J.J. Reynolds, *Biochem. J.*, 167 (1977) pp. 353–60.

Collagenase produced by normal human leukocytes or by normal human skin fibroblasts in cell cultures is purified by adsorption onto a collagen Sepharose 4B column. Prior to use in the assay, the zymogen is activated with trypsin, while the trypsin in turn, is inactivated with an excess of soybean trypsin inhibitor.

According to the assay procedure, microfuge tubes are prepared containing a total of about 150 µl. of solution containing: 25 µl. collagen ($^{14}$C-acetylated collagen—2 mg./ml in 0.01% acetic acid); 25 µl. of 0.15 M tris/0.015 M $CaCl_2$, pH 7.4; 75 µl. collagenase in tris buffer (0.05 M tris/0.005 M $CaCl_2$, pH 7.4); and 25 µl. of collagenase inhibitor in tris buffer. Samples and controls are incubated at 35° C. for one to five hours depending upon potency of the enzyme. At the end of the reaction period, the tubes are spun down in a Beckman Microfuge. A 25 µl. aliquot of each tube is then assayed in a scintillation counter. Since native collagen forms insoluble fibrils under these conditions, radioactivity detected in the supernate is a measure of collagen hydrolysis.

In a set of experiments, the compound of Example 1 is tested in the assay to determine its collagenase inhibition activity. In the first experiment, Collagen I (most predominant form of collagen, found in skin) is used as the substrate. The second experiment used Collagen II (which is found in cartilage) as the substrate. The results are summarized below:

| Experiment Number | $IC_{50}$ µM |
| --- | --- |
| 1 | 5.7 |
| 2 | 12.5 |

The results show that the compound tested is a potent inhibitor of collagenase, whose inhibitory activity shows no significant difference when tested with different collagen substrates.

EXAMPLE 3

The compound N-[[5-chloro-2-benzothiazolyl)thio]-phenylacetyl]-L-cysteine is tested for human elastase inhibition in an in vitro assay which is carried out as follows:

A crude elastase preparation is made by homogenizing human leukocyte granules [prepared according to the method of R. J. Baryk and J. Travis, *Biochemistry*, 15, (4), 837 (1976)], spinning and dialyzing the supernates against cold 0.05 M trisHCl/0.05 M Na Cl at a pH 8.0.

This elastase preparation is used in two assay methods to test for elastase inhibition.

Method 1

400 µl of the elastase preparation, 10 µl (0.0625 mg) of succinyl-L-alanyl-L-alanyl-L-alanyl-p-nitroanilide (the enzyme substrate), 207 µl of buffer and varying amounts of the elastase inhibitor under testing are incubated at 37° C. for 19 hours. The hydrolysis is measured by use of high pressure liquid chromatography (HPLC) or by the spectrophotometric measurement of the release of p-nitroaniline at a wavelength of 410 nm. In this method, the compound of Example 1 demonstrated an $IC_{50}$ of 2.1 µg/ml.

Method 2

In this method, the substrate used is an elastin-Congo red complex. Hydrolysis of this substrate by elastase releases Congo red, which is assayed by HPLC. The assay system also contains buffer and either 20 µg of the compound of Example 1, or no compound. The system is incubated at 37° C. for 18 hours. The standard sample represents the complete hydrolysis of the elastin-Congo red complex by hog pancreatic elastase.

| Sample Content | Relative Release of Congo Red |
| --- | --- |
| Standard | 1.0 |
| No Inhibitor | 0.104 |
| Compound of Example 1 | 0.000 |

The results of these assays show the strong inhibitory effect the compound of Example 1 exerts on the enzymatic activity of human leukocyte elastase.

What is claimed is:

1. A method of inhibiting mammalian elastase and collagenase in mammals afflicted with a disease state in which collagen-or elastin-containing tissue is broken down by elastase and/or collagenase, which comprises administering to such an afflicted mammal an amount sufficient to inhibit said elastase- and/or collagenase-induced collagen breakdown of an elastase and collagenase inhibitor having the formula

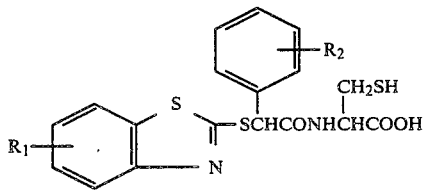

wherein $R_1$ is hydrogen, halo, nitro, amino, lower alkyl, lower alkoxy, trifluoromethyl or hydroxy; $R_2$ is fluorine, chlorine, bromine, lower alkyl, lower alkoxy, amino, nitro or trifluoromethyl; and the pharmacologically acceptable salts thereof.

2. The method of claim 1, wherein the inhibitor is N-[[(5-chloro-2-benzothiazolylthio)]phenylacetyl]-L-cysteine.

* * * * *